(12) United States Patent
Haiyan et al.

(10) Patent No.: US 10,870,620 B1
(45) Date of Patent: Dec. 22, 2020

(54) RADIOACTIVE CARBON-14-LABELED 2,2'-(((4-((4-14C CHLOROBENZYL)OXY)-3-METHOXYPHENYL)METHYLENE)BIS (2-HYDROXYETHYL)DITHIOACETAL, PREPARATION METHOD AND APPLICATIONS THERE OF

(71) Applicant: Zhejiang University, Hangzhou (CN)

(72) Inventors: Wang Haiyan, Hangzhou (CN); Lu Yuhui, Hangzhou (CN); Ye Qingfu, Hangzhou (CN)

(73) Assignee: Zhejiang University, Hangzhou (CN)

( * ) Notice: Subject to any disclaimer, the term of this patent is extended or adjusted under 35 U.S.C. 154(b) by 0 days.

(21) Appl. No.: 16/935,727

(22) Filed: Jul. 22, 2020

(30) Foreign Application Priority Data

Jul. 23, 2019 (CN) .......................... 2019 1 0666828

(51) Int. Cl.
| | |
|---|---|
| C07C 323/16 | (2006.01) |
| C07B 59/00 | (2006.01) |
| C07C 29/147 | (2006.01) |
| C07C 319/20 | (2006.01) |
| G01T 5/00 | (2006.01) |
| C07C 17/16 | (2006.01) |
| C07C 323/64 | (2006.01) |

(52) U.S. Cl.
CPC .......... *C07C 323/16* (2013.01); *C07B 59/001* (2013.01); *C07C 17/16* (2013.01); *C07C 29/147* (2013.01); *C07C 319/20* (2013.01); *C07C 323/64* (2013.01); *G01T 5/00* (2013.01); C07B 2200/05 (2013.01)

(58) Field of Classification Search
CPC ..... C07C 323/64; C07C 29/147; C07C 17/16; C07C 319/20; G01T 5/00; C07B 59/001; C07B 2200/05
See application file for complete search history.

(56) References Cited

FOREIGN PATENT DOCUMENTS

| | | |
|---|---|---|
| CN | 106467478 A | 3/2017 |
| CN | 108341839 A | 7/2018 |

OTHER PUBLICATIONS

Zhang et al. ("Facile Synthesis of Novel Vanillin Derivatives Incorporating a Bis(2-hydroxyethyl)dithioacetal Moiety as Antiviral Agents", Journal of Agricultural and Food Chemistry, vol. 65, May 2017, pp. 4582-4588).*
Office Action corresponding to Chinese Application No. 201910666828.3 dated Feb. 25, 2020.
Li, Ju-Ying , et al., ""A Review: Radiolabeled Synthesis of Pesticides"", Journal of Nuclear Agricultural Sciences 24(2):415-421 (2010).
Meng, Xin-Gang , et al., ""The Systemic Properties of XCLSBM in Tobacco Plant by UPLC-HRMS and Fluorescent Two-photon Confocal Microscope"", The 18th Annual Meeting of the Pesticides Institute, the Chemical Industry and Engineering Society of China [C], pp. 432-439 (2018).
Xu, Yajun , et al., ""Synthesis and analysis of carbon-14 labelled Dufulin with high specific activity"", Chinese Journal of Pesticide Science 19(6):672-678 (2017).
Yang, Zheng-Min, et al., ""Synthesis and Analysis of Carbon-14 Labelled Imidacloprid with High Specific Activity"", Journal of Nuclear and Radiochemistry 40(3):196-202 (Jun. 2018).

* cited by examiner

*Primary Examiner* — Rosalynd A Keys
(74) *Attorney, Agent, or Firm* — Myers Bigel, P.A.

(57) ABSTRACT

The present disclosure provides a radioactive carbon-14 labeled XCLSBM in the structure of Formula 4 and its preparation method and applications. A $^{14}C$ labeled raw material is used to synthesize a $^{14}C$-labeled XCLSBM, and a method for synthesizing a trace $^{14}C$-labeled marker of $^{14}C$-labeled XCLSBM is established, which avoids high-temperature, high-pressure reactions and the production process is safe with a low synthesis cost. The radioactive carbon-14 labeled XCLSBM can be used to trace the migration and transformation, metabolic degradation, absorption and enrichment of XCLSBM in environment and living bodies, for providing technical supports for comprehensive evaluation of the ecological safety of XCLSBM.

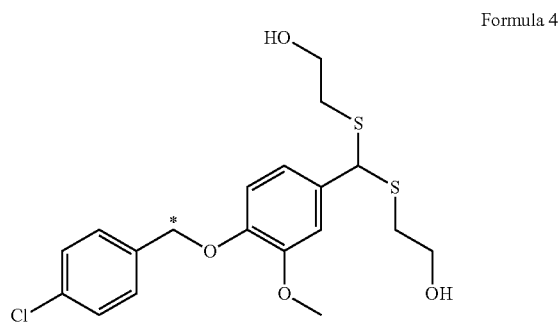

Formula 4

10 Claims, 2 Drawing Sheets

RADIOACTIVE CARBON-14-LABELED 2,2'-(((4-((4-14C CHLOROBENZYL)OXY)-3-METHOXYPHENYL)METHYLENE)BIS (2-HYDROXYETHYL)DITHIOACETAL, PREPARATION METHOD AND APPLICATIONS THERE OF

STATEMENT OF PRIORITY

This application claims priority from and the benefit of Chinese Patent Application No. 201910666828.3, filed on Jul. 23, 2019, the disclosure of which is hereby incorporated herein in its entirety.

FIELD OF THE INVENTION

The present disclosure relates to the field of radioactive chemical synthesis, and particularly relates to a radioactive carbon-14 labeled 2,2'-(((4-((4-chlorobenzyl)oxy)-3-methoxyphenyl)methylene)bis(2-hydroxyethyl) dithioacetal, a preparation method and applications thereof.

BACKGROUND OF THE INVENTION

Vanillin (4-hydroxy-3-methoxybenzaldehyde, CAS registration number: CN106467478A) is an important natural product with biological safety, simple structure and good biological activity, which is widely used in the field of new drug development and lead compound for agriculture applications. Antiviral drugs based on natural products have greater advantages than synthetic chemical drugs, such as low toxicity, environmental friendliness, easily being decomposed and unique action modes. The 2,2'-(((4-((4-chlorobenzyl)oxy)-3-methoxyphenyl)methylene)bis(2-hydroxyethyl) dithioacetal is abbreviated as XCLSBM, which is a compound synthesized by introducing bis(2-hydroxyethyl) dithioacetal fragments into vanillin. This compound is a candidate drug for plant immune activators and has a significant effect in controlling plant mosaic virus, but it is still in the basic research stage. Its underlying mechanism is also unclear, and no research has been reported on the study of environmental behavior of XCLSBM. Countries and organizations such as the European Union, the United States, and the OECD clearly require the provision of information on metabolic degradation products during the environmental safety assessment of pesticides, and have formulated corresponding standard operating procedures specifically for this purpose. These standard operating procedures all states that: pesticides metabolic degradation research firstly needs to consider the isotope tracing method, while the radioactive carbon-14 labeled XCLSBM is the tracer necessary for tracing and studying its environmental behavior. At present, there is no report on the synthesis of XCLSBM marker at home and abroad.

SUMMARY OF THE INVENTION

The present disclosure aims at overcoming the shortcomings and deficiencies in existing technologies, which provides a radioactive carbon-14 labeled 2,2'-(((4-((4-$^{14}$C chlorobenzyl)oxy)-3-methoxyphenyl)methylene) bis (2-hydroxyethyl) dithioacetal (which is referred as XCLSBM in the following parts) by using isotopic labeling techniques and modem instrument analysis technology, also provides its preparation method and applications. The $^{14}$C-labeled raw material is used to synthesize a $^{14}$C-labeled XCLSBM, and a method for synthesizing a trace amount $^{14}$C-labeled marker of $^{14}$C-labeled XCLSBM is established, which avoids high-temperature, high-pressure reactions, and the production process is safe with a low synthesis cost. The radioactive carbon-14 labeled XCLSBM can be used to track the migration and transformation, metabolic degradation, absorption and enrichment of XCLSBM in environment and living bodies, for providing technical supports for comprehensive evaluation of the ecological safety of XCLSBM.

The object of the present disclosure is achieved by the following technical solution: a radioactive carbon-14 labeled XCLSBM, which is 2,2'-(((4-((4-$^{14}$C chlorobenzyl) oxy)-3-methoxyphenyl)methylene)bis(2-hydroxyethyl) dithioacetal, its structural formula is shown as Formula 4:

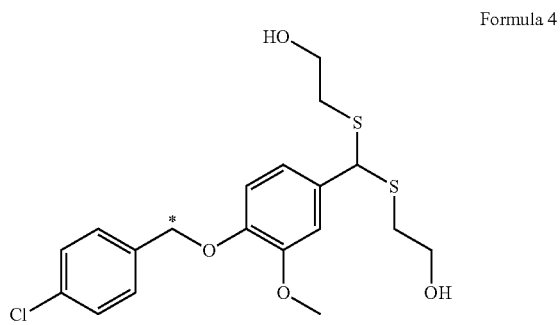 [SMILES: COc1cc(C(SCCO)SCCO)ccc1OCc1ccc(Cl)cc1]

Formula 4

Wherein, the asterisk represents the position of the carbon-14 mark, i.e. * represents $^{14}$C.

The method for synthesizing a radioactive carbon-14 labeled XCLSBM includes the following steps:
1) using p-chlorobenzoyl[$^{14}$C] formic acid of Formula 1 as a radioactive raw material, adding tetrahydrofuran and a red aluminum-containing toluene solution to obtain p-chlorobenzoyl[$^{14}$C] methanol of Formula 2 through a reduction reaction;
2) the p-chlorobenzoyl[$^{14}$C] methanol of Formula 2 is brominated with phosphorus tribromide to obtain a p-chlorobenzoyl[$^{14}$C] methyl bromide of Formula 3;
3) the p-chlorobenzoyl[$^{14}$C] methyl bromide of Formula 3 is reacted with bis(2-hydroxyethyl) dithioacetal-containing vanillin under alkaline conditions through an electrophilic substitution reaction to obtain the target labeled crude product of Formula 4, which is then purified by a reversed-phase high-performance liquid chromatography (RP-HPLC) to give the radioactive carbon-14 labeled XCLSBM of Formula 4. The total yield of the radio-synthesis reaction is 13%. The product structure is characterized and confirmed by nuclear magnetic resonance hydrogen spectroscopy, mass spectrometry and online radioactive high performance liquid chromatography (HPLC-FSA) analysis.

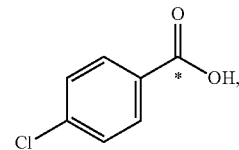

1

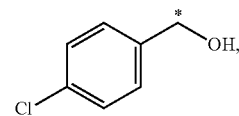

2

-continued

3

[Chemical structure: 4-chlorobenzyl bromide with *CH₂Br]

4

[Chemical structure showing the coupled product with *=¹⁴C labels]

* = ¹⁴C

And the bis(2-hydroxyethyl) dithioacetal-containing vanillin has the following structure:

[Chemical structure of bis(2-hydroxyethyl) dithioacetal-containing vanillin]

In step 1), the ratio of the amount of p-chlorobenzoyl[$^{14}$C] formic acid to the red aluminum-containing toluene solution is 0.78 mmol: 1.5~3 mL, most preferably 0.78 mmol: 2.34 ml. The red aluminum [2H-bis(2-methoxyethoxy) sodium aluminate)] is dissolved in toluene to give a red aluminum-containing toluene solution.

The reduction reaction conditions are that at 15 to 35° C. for a period of 12 to 20 hours, more preferably 20 to 30° C. for a period of 14 to 18 hrs, and most preferably 25° C. for 16 hrs.

In step 2), the molar ratio of phosphorus tribromide to p-chlorobenzoyl[$^{14}$C] methanol of Formula 2 is 1: 2~4; more preferably, the molar ratio of phosphorus tribromide to p-chlorobenzoyl[$^{14}$C] methanol of Formula 2 is 1:3;

The bromination reaction between p-chlorobenzoyl[$^{14}$C] methanol of Formula 2 and phosphorus tribromide includes the steps of:

adding p-chlorobenzoyl[$^{14}$C] methanol to a reactor, performing an atmosphere replacement with nitrogen, injecting dichloromethane thereto, then adding dimethylformamide in dropwise; after cooling down by an ice salt bath, adding dichlorosulfoxide, followed by raising the temperature to 15~35° C. to carry out the chlorination reaction for 2~4 hrs, further preferably raising the temperature to 25° C. to carry out the chlorination reaction for 3 hrs; after completing the chlorination reaction, adding water to quench the reaction, extracting with dichloromethane, combining organic phases, adding tribromide phosphorus, reacting with phosphorus tribromide, drying with anhydrous magnesium sulfate, then filtering and carrying out a rotary evaporation under reduced pressure to obtain p-chlorobenzoyl[$^{14}$C] methyl bromide of Formula 3.

The ratio of the amount of p-chlorobenzoyl[$^{14}$C] methanol, dichloromethane, dimethylformamide, and dichlorosulfoxide is 0.45 mmol: 1~5 mL: 1~4 drops: 80~130 mg, most preferably the ratio of the amount of p-chlorobenzoyl [$^{14}$C] methanol, dichloromethane, dimethylformamide and dichlorosulfoxide is 0.45 mmol: 3 mL: 2 drops: 106 mg.

In step 3), the alkaline condition is established by using potassium hydroxide.

The molar ratio of p-chlorobenzoyl[$^{14}$C] methyl bromide of Formula 3, bis(2-hydroxyethyl) dithioacetal-containing vanillin, and potassium hydroxide is 1:0.8~1.2:0.8~1.2. More preferably, the molar ratio of p-chlorobenzoyl[$^{14}$C] methyl bromide of Formula 3, bis(2-hydroxyethyl) dithioacetal-containing vanillin, and potassium hydroxide is 1:1:1.

The purification by the reversed-phase high-performance liquid chromatography applies a petroleum ether-ethyl acetate system with a volume ratio of 20:1~4:1 to perform the column chromatography purification.

The radioactive carbon-14 labeled XCLSBM can be used to track the migration and transformation, metabolic degradation, absorption and enrichment of XCLSBM in environment and living bodies, for providing technical supports for comprehensive evaluation of the ecological safety of XCLSBM.

In comparison with prior arts, the present disclosure has the following advantages:

(1) The carbon-14 labeled XCLSBM synthesized by the present disclosure has been analyzed by radioactive thin layer imaging (TLC-IIA), high performance liquid chromatography-liquid scintillation counter analysis (HPLC-LSC), and online radioactive high efficiency liquid phase chromatography/photo-diode array/mass spectrometry (HPLC-FSA/PDA/MS) and LSC analysis, which demonstrate that the radiochemical purity and chemical purity of the [$^{14}$C]-XCLSBM are both greater than 95%, and its specific activity is 15.75 mCi/mmol. The nuclide carbon-14 is positioned on a relatively stable skeleton of XCLSBM and not easy to be lost, which makes it can be used to trace and study the pollution evolution patterns of migration and transformation, metabolic degradation, absorption and enrichment and the like of XCLSBM in the environment and organisms.

(2) No document has been reported for providing a synthetic technical route of [$^{14}$C]-XCLSBM at present, while the synthetic technical route of the present disclosure involves mild reaction conditions without any high-temperature and high-pressure reactions, thereby no needs of pressure-resistant synthetic instrument and equipment. The experimental operations of the present disclosure are convenient and safe with simple synthesis conditions.

DETAILED DESCRIPTION OF THE INVENTION

The present disclosure provides a radioactive carbon-14 labeled XCLSBM, which is 2,2'-(((4-((4-$^{14}$C chlorobenzyl)oxy)-3-methoxyphenyl)methylene)bis(2-hydroxyethyl) dithioacetal, the structural formula is shown as Formula 4:

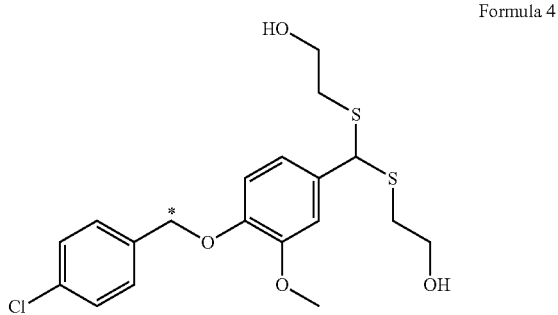 [SMILES: COc1cc(C(SCCO)SCCO)ccc1OCc1ccc(Cl)cc1]

Formula 4

Wherein, the asterisk represents the position of the carbon-14 mark.

Figure 1:
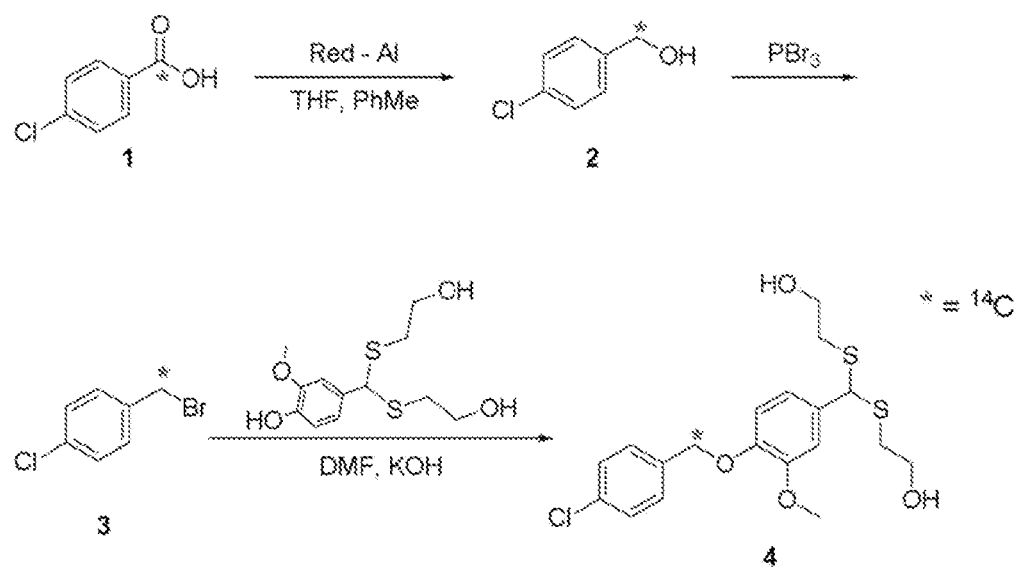
FIG. 1 is a synthetic technical route illustration of the [$^{14}$C]-XCLSBM (4) according to the present disclosure.

As shown in FIG. 1, it is the method for synthesizing a radioactive carbon-14 labeled XCLSBM, including the following steps:

Taking a 25 mL of dry three-necked bottle, adding p-chlorobenzoyl[$^{14}$C] formic acid (the structure of Formula 1, SMSJ181157E: 123.4 mg, 0.78 mmol) into it, performing an atmosphere replacement with nitrogen for three times, and then injecting 4 mL of dry tetrahydrofuran (THF) thereto; then cooling down by an ice salt bath for 10 mins, slowly adding 2.34 mL of red aluminum in dropwise (2~3 s/drop, the solvent was toluene); after finishing the addition, raising the temperature to room temperature of 25° C. normally and carrying out the reaction for 16 hrs. After completing the reaction, slowly adding water to quench the reaction, transferring the reaction solution to a spinner flask, evaporating and removing the solvent; then adding ethyl acetate and extracting, combing organic phases, drying with anhydrous magnesium sulfate, then filtering and carrying out a rotary evaporation under reduced pressure to obtain a crude product, followed by column chromatography (PE:EA=20:1~10:1) to form a white solid compound (the structure of Formula 2, 63.8 mg), PE:EA=10:1, $R_f$=0.8, the reaction yield is 57%. PE is an abbreviation for petroleum ether, and EA refers to ethyl acetate. The $R_f$ value is the ratio of the distance the substance traveling on the silica gel chromatography plate and the distance of the solvent line, which can be used to determine whether the target product is produced.

Taking a 25 mL of dry three-neck flask, adding p-chlorobenzoyl[$^{14}$C] methanol (the structure of Formula 2, 63.8 mg, 0.45 mmol) into it, performing an atmosphere replacement with nitrogen for three times, injecting 3 mL of dry dichloromethane thereto and then adding 2 drops of dimethylformamide (DMF); after cooling down by an ice salt bath for 10 mins, adding 106 mg of dichlorosulfoxide and then raising the temperature to room temperature of 25° C. and carrying out the reaction for 3 hrs. After completing the reaction, slowly adding water to quench the reaction, extracting with dichloromethane, combing organic phases, adding phosphorus tribromide with a molar ratio of 1:3 for phosphorus tribromide of the structure of Formula 2 to p-chlorobenzoyl[$^{14}$C] methanol; reacting with phosphorus tribromide, drying with anhydrous magnesium sulfate, filtering, and carrying out a rotary evaporation under reduced pressure to obtain the target product compound as light brown oil p-chlorobenzoyl[$^{14}$C]methyl bromide (the structure of Formula 3, 70 mg), the volume ratio of PE:EA=10:1, $R_f$=0.8. The reaction yield is 97%.

In a dry three-neck flask (25 mL), sequentially adding the substrate bis(2-hydroxyethyl) dithioacetal-containing vanillin and potassium hydroxide (KOH), performing an atmosphere replacement with nitrogen for three times, injecting dry DMF, acetonitrile (with a volume ratio of 1:1) by an injector to dissolve the compound of Formula 3, the molar ratio of p-chlorobenzoyl[$^{14}$C] methyl bromide of Formula 3, bis(2-hydroxyethyl) dithioacetal-containing vanillin and potassium hydroxide is 1:1:1; then raising the temperature to 50° C., carrying out the reaction under stirring, and monitoring the reaction procedure by TLC (PE:EA=4:1, V/V; R/=0.4); the reaction was completed in about 16 hrs. After completing the reaction, cooling down the reaction solution to a room temperature of 25° C.; transferring the reaction solution to a spinner flask and concentrating to remove the solvent; after concentration, adding 5 mL of water, 3 drops of 20 wt. % of sodium hydroxide solution, extracting with ethyl acetate, combing organic phases, then concentrating under reduced pressure to remove the solvent and obtain a crude product; the crude product was purified by column chromatography (PE:EA=20:14:1) to form a white solid (Formula 4, 95.2 mg). The reaction yield was 80%. The chromatographic conditions are shown in Table 1 below:

TABLE 1

| HPLC mobile phase conditions of XCLSBM | | | |
|---|---|---|---|
| Time (min) | Flow Rate (mL/min) | methanol (%) | water (%) |
| 0.01 | 10 | 60 | 40 |
| 5.00 | 10 | 60 | 40 |
| 15.00 | 10 | 80 | 20 |
| 20.00 | 10 | 100 | 0 |
| 25.00 | 10 | 100 | 0 |
| 27.00 | 10 | 60 | 40 |
| 30.00 | 10 | 60 | 40 |

Figure 2:
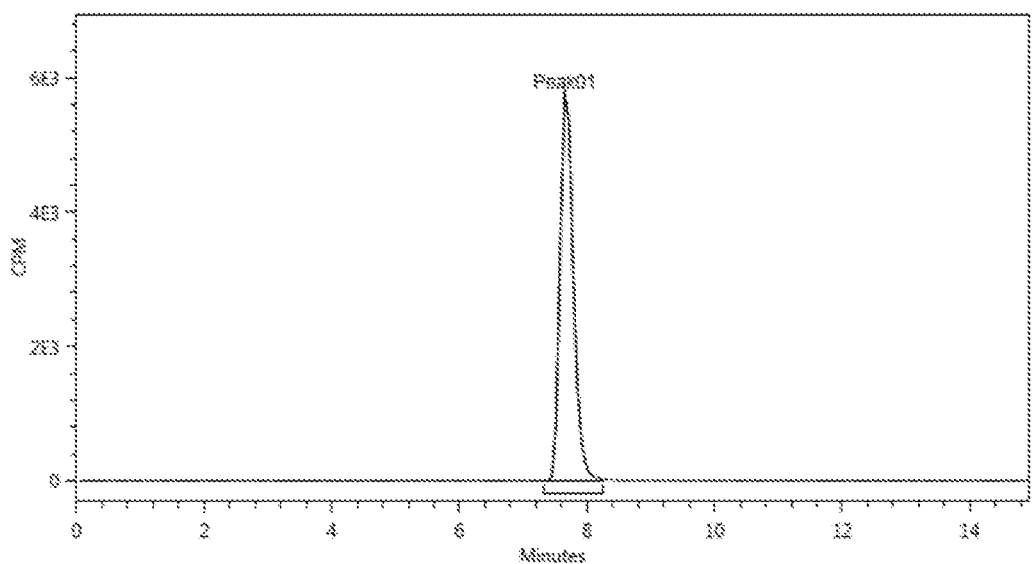
FIG. 2 is a radiographic chromatogram (HPLC-FSA) of the [$^{14}$C]-XCLSBM according to the present disclosure, i.e. the flow scintillation quantification diagram of the XCLSBM analyzed by a flow scintillation analyzer-liquid chromatography.

FIG. 2 is a radiographic chromatogram (HPLC-FSA) of the [$^{14}$C]-XCLSBM according to the present disclosure, i.e. the flow scintillation quantification diagram of the XCLSBM analyzed by a flow scintillation analyzer-liquid chromatography.

Figure 3:
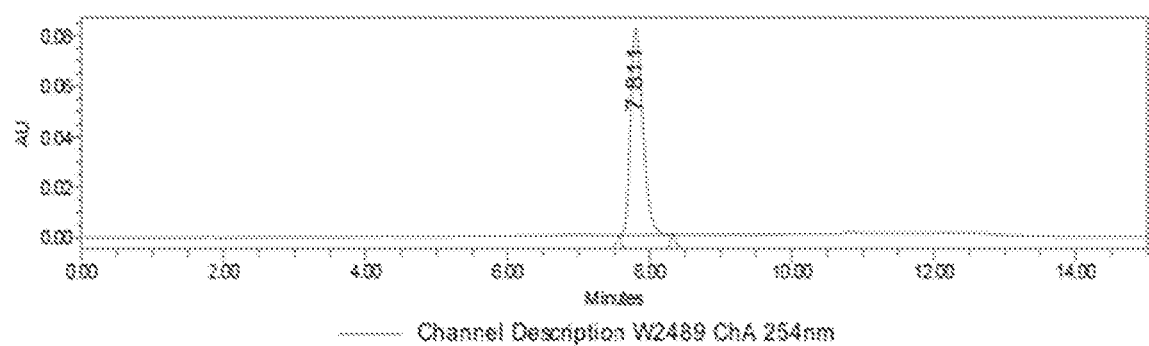
FIG. 3 is a chromatogram (HPLC-UV, 254 nm) of the [$^{14}$C]-XCLSBM according to the present disclosure, i.e. the peak time of the liquid chromatographic peak of the radioactive synthetically labeled pesticide XCLSBM under the wavelength of 254 nm is 7.811 mins.
Figure 4:
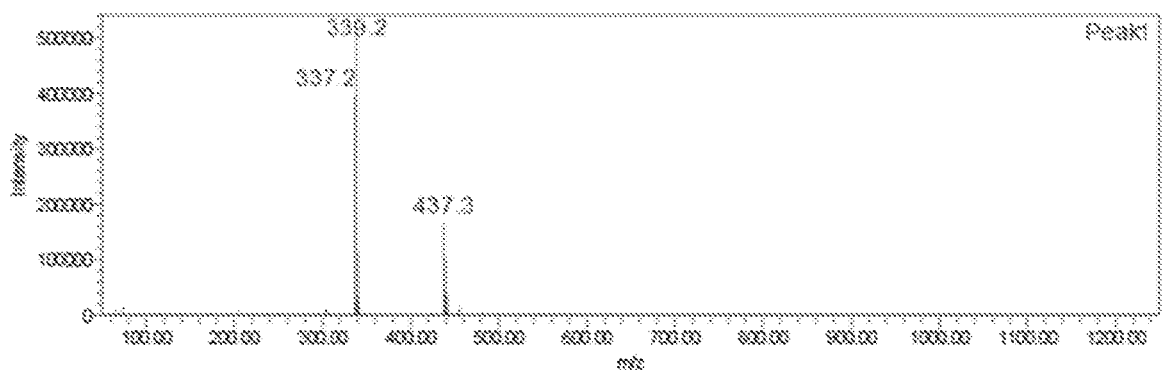
FIG. 4 is a mass spectrogram (ESI(+)-MS) of the [$^{14}$C]-XCLSBM according to the present disclosure, i.e. the quasi-molecular ion peak [M+Na] mass spectrum of the XCLSBM.

FIG. 3 is a chromatogram (HPLC-UV, 254 nm) of the [$^{14}$C]-XCLSBM according to the present disclosure, i.e. the peak time of the liquid chromatographic peak of the radioactive synthetically labeled pesticide XCLSBM under the wavelength of 254 nm is 7.811 mins;

FIG. 4 is a mass spectrogram (ESI(+)-MS) of the [$^{14}$C]-XCLSBM according to the present disclosure, i.e. the quasi-molecular ion peak [M+Na] mass spectrum of the XCLSBM, which indicates that the final product has the structure of Formula 4.

The final product structure is characterized and confirmed by nuclear magnetic resonance hydrogen spectroscopy, mass spectrometry and online radioactive high performance liquid chromatography (HPLC-FSA) analysis.

The radioactive carbon-14 labeled XCLSBM can be used to trace the migration and transformation, metabolic degra- That which is claimed:

1. A radioactive carbon-14-labeled XCLSBM, characterized in that the chemical name is 2,2'-(((4-(4-$^{14}$C chlorobenzyl)oxy)-3-methoxyphenyl)methylene)bis (2-hydroxyethyl) dithioacetal, the structural formula is shown as Formula 4:

Formula 4 wherein the asterisk represents the position of the carbon-14 mark.

2. A method for preparing the radioactive carbon-14 labeled XCLSBM of claim 1, characterized in that comprising the following steps:
1) using p-chlorobenzoyl[$^{14}$C] formic acid of Formula 1 as a radioactive raw material, adding tetrahydrofuran and a red aluminum-containing toluene solution to obtain p-chlorobenzoyl[$^{14}$C] methanol of Formula 2 through a reduction reaction;
2) the p-chlorobenzoyl[$^{14}$C] methanol of Formula 2 is brominated with phosphorus tribromide to obtain a p-chlorobenzoyl[$^{14}$C] methyl bromide of Formula 3;
3) the p-chlorobenzoyl[$^{14}$C] methyl bromide of Formula 3 is reacted with bis(2-hydroxyethyl) dithioacetal-containing vanillin under alkaline conditions through an electrophilic substitution reaction to obtain the target labeled crude product of Formula 4, which is then purified by a reversed-phase high-performance liquid chromatography to give the radioactive carbon-14 labeled XCLSBM of Formula 4,

1

2

3

4

* = $^{14}$C and the bis(2-hydroxyethyl) dithioacetal-containing vanillin has the following structure:

3. The method for preparing the radioactive carbon-14 labeled XCLSBM of claim 2, characterized in that in step 1), the ratio of the amount of p-chlorobenzoyl[$^{14}$C] formic acid to the red aluminum-containing toluene solution is 0.78 mmol: 1.5~3 mL.

4. The method for preparing the radioactive carbon-14 labeled XCLSBM of claim 2, characterized in that in step 1), the reduction reaction conditions are that reacting at 15~35° C. for 12~20 hrs.

5. The method for preparing the radioactive carbon-14 labeled XCLSBM of claim 2, characterized in that in step 2), the molar ratio of phosphorus tribromide to p-chlorobenzoyl [$^{14}$C] methanol of Formula 2 is 1:2~4.

6. The method for preparing the radioactive carbon-14 labeled XCLSBM of claim 2, characterized in that in step 2), the bromination reaction between p-chlorobenzoyl[$^{14}$C] methanol of Formula 2 and phosphorus tribromide specifically comprising the steps of:
adding p-chlorobenzoyl[$^{14}$C] methanol to a reactor, performing an atmosphere replacement with nitrogen, injecting dichloromethane thereto, then adding dimethylformamide in dropwise; after cooling down by an ice salt bath, adding dichlorosulfoxide, followed by raising the temperature to 15~35° C. to carry out the chlorination reaction for 2~4 hrs; after completing the chlorination reaction, adding water to quench the reaction, extracting with dichloromethane, combining organic phases, adding phosphorus tribromide, reacting with phosphorus tribromide, drying with anhydrous magnesium sulfate, then filtering and carrying out a rotary evaporation under reduced pressure to obtain p-chlorobenzoyl[$^{14}$C] methyl bromide of Formula 3.

7. The method for preparing the radioactive carbon-14 labeled XCLSBM of claim 2, characterized in that in step 3), the alkaline condition is established by using potassium hydroxide.

8. The method for preparing the radioactive carbon-14 labeled XCLSBM of claim 7, characterized in that in step 3), the molar ratio of p-chlorobenzoyl[$^{14}$C] methyl bromide of Formula 3, bis(2-hydroxyethyl) dithioacetal-containing vanillin and potassium hydroxide is 1:0.8~1.2:0.8~1.2.

9. The method for preparing the radioactive carbon-14 labeled XCLSBM of claim 2, characterized in that in step 3), the purification by the reversed-phase high-performance liquid chromatography applies a petroleum ether-ethyl acetate system with a volume ratio of 20:1~4:1 to perform the column chromatography purification.

10. A method of tracing and tracking the XCLSBM in an environment utilizing the radioactive carbon-14 labeled XCLSBM of claim 1.

\* \* \* \* \*

UNITED STATES PATENT AND TRADEMARK OFFICE
CERTIFICATE OF CORRECTION

PATENT NO. : 10,870,620 B1
APPLICATION NO. : 16/935727
DATED : December 22, 2020
INVENTOR(S) : Haiyan et al.

Page 1 of 1

It is certified that error appears in the above-identified patent and that said Letters Patent is hereby corrected as shown below:

On the Title Page

Item (54) Title: Please correct "THERE OF" to read -- THEREOF --

Item (30) Foreign Application Priority Data: Please correct "2019 1 0666828" to read -- 2019 1 0666828.3 --

In the Specification

Column 1, Line 6: Please correct "THERE OF" to read -- THEREOF --

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*